United States Patent [19]

Artzt et al.

[11] 4,195,345

[45] Mar. 25, 1980

[54] METHOD AND APPARATUS FOR DETECTING THE FAULTY WORKING OF SPINNING UNITS OF OPEN-END SPINNING MACHINES

[75] Inventors: Peter Artzt, Pfullingen; Gerhard Egbers; Rolf Guse, both of Reutlingen; Sohrab Tabibi, Pfullingen, all of Fed. Rep. of Germany

[73] Assignee: Schubert & Salzer, Ingolstadt, Fed. Rep. of Germany

[21] Appl. No.: 767,997

[22] Filed: Feb. 11, 1977

[30] Foreign Application Priority Data

Feb. 13, 1976 [DE] Fed. Rep. of Germany ....... 2605737

[51] Int. Cl.² ............... D01H 13/22; G06F 15/46
[52] U.S. Cl. ........................... 364/470; 57/81; 57/264; 57/362; 73/160; 364/552
[58] Field of Search .............. 364/470, 552, 554, 563; 57/34 R, 81, 156, 264, 362; 73/159, 160; 235/92 DN, 92 PD; 28/185, 187

[56] References Cited

U.S. PATENT DOCUMENTS

| 4,007,457 | 2/1977 | Aeppli | 57/34 R |
|---|---|---|---|
| 4,051,722 | 10/1977 | Feller | 364/552 X |
| 4,056,926 | 11/1977 | Stuber | 57/81 |
| 4,058,962 | 11/1977 | Spescha et al. | 57/156 X |
| 4,060,965 | 12/1977 | Schwartz | 57/34 R |

*Primary Examiner*—Jerry Smith
*Attorney, Agent, or Firm*—Bailey, Dority & Flint

[57] ABSTRACT

A method and apparatus for detecting the faulty working of spinning units of an open-end spinning machine by monitoring the faults in yarn as it is fed from the spinning machine. An electrical signal is produced by a sensor indicating faults appearing in the yarn. Another signal of predetermined frequency corresponding to the speed of delivery of the yarn from the spinning machines is generated. The electrical signal produced by the sensor is electrically multiplied by the signal of predetermined frequency for producing a differential signal. This differential signal is filtered, shaped and integrated and subsequently compared with a preset threshold value for producing a signal indicating when the occurrence of faults exceed a predetermined threshold. This signal can be used for stopping the spinning unit.

19 Claims, 3 Drawing Figures

METHOD AND APPARATUS FOR DETECTING THE FAULTY WORKING OF SPINNING UNITS OF OPEN-END SPINNING MACHINES

BACKGROUND OF THE INVENTION

It is generally known in the spinning industry that, apart from the unevenness in the yarn, which may have the most varied amplitudes, periodic deviations occur which later become clearly visible in the yarn (yarn conversion table) and also in the woven fabric as a result of their position side by side. This phenomenon is generally known as the moire effect. The causes of such periodic faults in the yarn originate from the processing during which disturbances periodically occur. In a ring spinning frame, such disturbances may occur, for example, as a result of drawing rollers beating. During open end or rotor spinning, such disturbances appear particularly strikingly as a result of deposits in the rotor. Because it is known what generally causes the periodic disturbances, conclusions regarding the source of distrubance can be drawn from a yarn-unevenness diagram.

In open-end spinning, with regard to moire detection, it is known that the visible spacing of thick places appear on the yarn according to the circumference of the rotor. The difficulty in detection, however, lies in the fact that the delivery speed is variable and so the moire frequency is likewise variable.

It is true that it is possible to check a yarn production afterwards by random samples by means of a spectrograph (Uster) for whether such a moire effect has appeared or not. This often results in a major loss since the production has already taken place and, in any case, a relatively large amount of faulty yarn may have been produced depending on the frequency of the checking.

It is true that it is already known to detect the point of disturbance directly and immediately by monitoring individual spindles and so to avoid a large faulty production (DT-OS No. 2.409.882). According to the earlier proposal, this is effected so that, by measuring the yarn cross-section or yarn diameter, an electrical signal is produced which is subjected to an evaluation by means of at least one non-linear correction member.

In order to detect periodic faults in the spun yarn it is necessary, in this case, to convey the signal originating from a monitored yarn through electric filters which are adjusted to the expected repetition frequency of these faults, hereinafter termed moire frequency, and a detector has to be present at each spinning station. Since the delivery speed of the spun yarn is variable, either narrow-band filters have to be used, which are variable in their midband frequency, which leads to considerable costs, or very wide-band filters have to be used so that the moire frequency is transmitted by them even at different yarn delivery speeds. In the latter case, it is true that the costs for the circuit arrangement are reduced somewhat, nevertheless the wide-band nature of the filters has the effect that a considerable proportion of the frequencies of the normal unevenness of the spun yarn can pass through. When wide-band filters are used, therefore, a moire effect is only detected if it stands out very clearly from the normal unevenness of the yarn.

SUMMARY OF THE INVENTION

According to the invention, this problem is solved in that the yarn signal obtained is electrically multiplied by a signal of predetermined frequency, which is derived from the spinning machine and the differential-frequency signal thus obtained is filtered and subjected to a pulse shaping. The shaped pulse train is then integrated and compared with a preset threshold value. The signal of predetermined frequency is a rectangular signal which has the advantage that it is simple to produce and renders possible a simple multiplication by actuation of an on/off switch. The frequency of the rectangular signal may appropriately be derived from the speed of rotation of the yarn delivery roller. In order to better detect the frequency variations in the yarn signal, for example, as a result of slip of the yarn, the frequency of the rectangular signal is periodically altered. In one embodiment, the frequency of the rectangular signal is inexpensively altered mechanically. In another embodiment as a result of the fact that the frequency of the rectangular signal is altered electronically, external influences are eliminated.

In order to increase the certainty of detecting a moire effect, the filtered differential-frequency signal is compared with a second threshold value before the pulse shaping. The amplitude of the second threshold value is derived from the yarn signal, as a result of which the method can be used for a wider range of yarn counts. Its use for a wider range of speeds in the yarn delivery is rendered possible by the fact that the amplitude of the second threshold value is derived from the speed of rotation of the yarn delivery roller.

The advantage of a greater certainty of detection for a wider range of counts and a wider range of yarn delivery speeds also results from the fact that the amplitude of the threshold value with which the integrated differential-frequency signal is compared, is derived from the speed of rotation of the yarn delivery roller. The yarn signal is preferably obtained by measuring the yarn dimensions over the yarn tension.

The apparatus for carrying out the method, which is equipped with a measurement receiver, is characterized by a signal generator, a multiplier, a filter, a pulse shaper, an integrator and a comparator. The signal generator may appropriately consist of a perforated disc connected to the yarn delivery roller, with a light source and photoelectric cell associated therewith. In another embodiment the signal generator consists of a slotted disc with associated magnetic receiver. The periodic alteration of the frequency of the rectangular signal by mechanical means is achieved by connecting the perforated disc or slotted disc to the yarn delivery roller through a cone gear. The provision of a a frequency-voltage converter, a delta-voltage generator, an adding amplifier and a voltage-frequency converter renders possible the electronic alteration of the frequency of the rectangular signal. In order to increase the certainty of detecting a moire effect, a second comparator is connected between the filter and the pulse shaper.

Accordingly, it is an object of the present invention to provide a method and apparatus for determining when components of a spinning machine are not functioning properly.

Another important object of the present invention is to provide an apparatus for monitoring the yarn being produced on open-end spinning machines for detecting the faulty working of spinning units and, in particular, the spinning compartment.

Still another important object of the present invention is to provide a method and apparatus which renders possible, in a simple manner, a reliable detection of periodically reoccuring faults in the spun yarn and, hence, faulty working of the spinning unit of an open end spinning machine.

These and other objects and advantages of the invention will become apparent upon reference to the following specification, attendant claims, and drawings.

DESCRIPTION OF A PREFERRED EMBODIMENT

Figure 1:
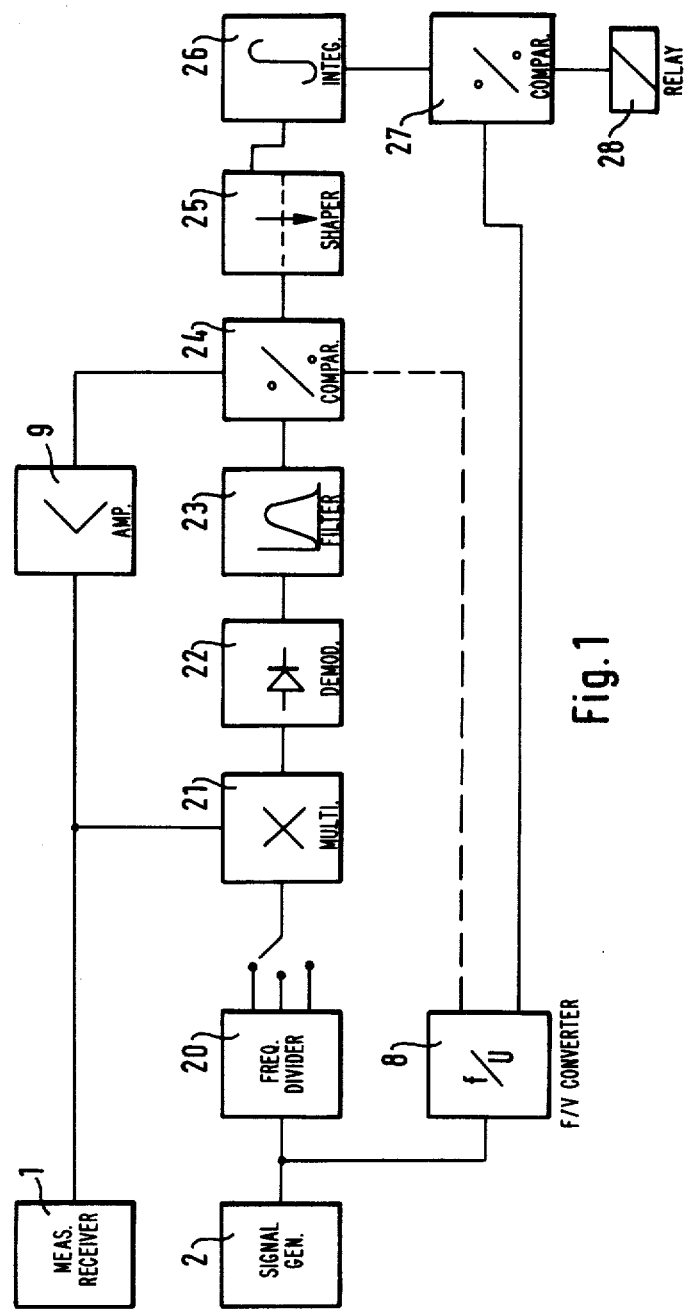
FIG. 1 shows the block circuit diagram of the apparatus according to the invention.

The monitoring apparatus illustrated as an example of an embodiment in FIG. 1 contains a measurement receiver 1 which converts a measured value obtained by sensing the yarn into an electric signal which is hereinafter called the yarn signal. The yarn signal is preferably produced by measuring the yarn mass via the yarn tension and converting it into an electric signal. For this purpose, the measurement receiver 1, which is not illustrated in detail, comprises two parallel coils, in the stray field of which there is movable a yarn sensor constructed in the form of a plate-spring, for example, gripped at one side, the natural frequency of which is lower than the lowest rotational frequency of the rotor of the open-end spinning apparatus and which exerts a pressure on the spun yarn in the region between the rotor and the yarn winding point. Such a device, by means of which the yarn mass if measured via the yarn tension using the centrifugal force acting on the yarn, and a measured value is produced therefrom, is known, so that a further explanation can be dispensed with.

Instead of the yarn mass, however, the yarn diameter or yarn cross-section may possibly be measured by well-known devices and the measured value obtained be converted into an electric signal.

The yarn signal originating from the measurement receiver 1 passes through an amplifier (not shown) and is then evaluated by a search-frequency process which utilizes a signal generator 2 that produces a signal of predetermined frequency derived from the moire frequency. The signal of predetermined frequency is preferably a rectangular signal which is simple to produce. When the rectangular signal from generator 2 and the yarn signal from sensor 1 are multiplied by one another, as will be explained later, frequencies result which correspond to the sum and the difference of the frequency proportions of the two signals. If a suitable frequency of the rectangular signal is selected, a filter adjusted to a fixed differential frequency can be used for the moire detection, even with a variable moire frequency, for example, at different yarn delivery speeds, which is an advantage for reasons of price.

The frequency of the rectangular signal is derived from the speed of rotation of the machine, only those rotating machine parts being considered which ensure that the frequency of the rectangular signal differs only slightly from the moire frequency. Preferably, therefore, the speed of rotation of the yarn-delivery roller, which—apart from the slip between roller and yarn—is in a fixed ratio to the moire frequency, is used to produce the rectangular signal. Furthermore, since it is a requirement that the method and the apparatus should be able to be used for a plurality of yarn-delivery speeds and yarn counts, while on the other hand, with this requirement, it is not possible, because of different yarn slip, to maintain the differential frequency between rectangular signal and moire frequency so constant that it comes with sufficient certainty within the pass range of the following filter, a device is provided which enables the frequency of the rectangular signal to be allowed to swing about a mean value. In this manner, at any yarn-delivery speed and with any yarn slip which usually occurs, the differential frequency passes periodically through the pass range of the following filter.

Figure 2:
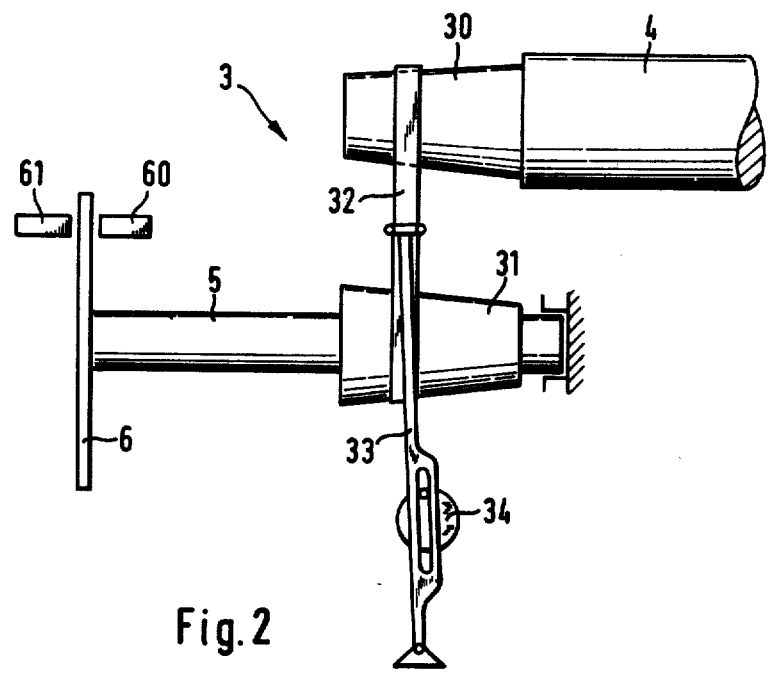
FIG. 2 shows an apparatus for the mechanical alteration of the frequency of the rectangular signal.

FIG. 2 shows a device for producing and periodically altering the frequency of the rectangular signal by mechanical means. A truncated cone 30 of a cone gear 3 which is connected to the yarn-delivery roller 4 for rotation therewith, is situated opposite a truncated cone 31 secured to a shaft 5 mounted for rotation in the machine frame. A drive belt 32 runs over the truncated cones 30 and 31. The position of the drive belt 32 and, hence, the transmission ratio, is continuously altered by an eccentric rod 33 with associated eccentric 34, which is continuously driven by a motor (not shown). Rigidly connected to the drive shaft 5 is a perforated disc 6, so that light pulses from a light source 60 can be transmitted to a photoelectric cell 61. The photoelectric cell 61 is electrically connected to a frequency divider 20 (FIG. 1). With suitable selection of the basic transmission ratio, the number of holes in the perforated disc 6 and the reduction ratio of the frequency divider 20 connected to the photoelectric cell 61 (FIG. 1), a pulse train results, the frequency of which corresponds approximately to the moire frequency. This frequency is periodically altered within narrow limits by the variable speed gearing. Instead of the perforated disc 6, other pulse producers, for example, a slotted disc with a magnetic receiver (not shown) associated therewith may also be used.

Figure 3:
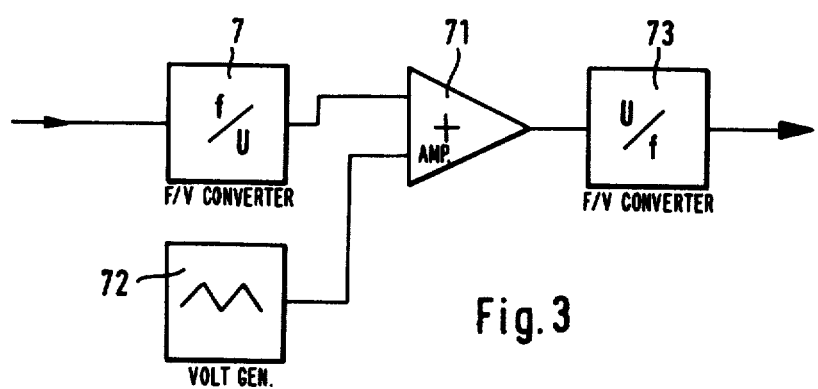
FIG. 3 shows the block circuit diagram of a device for the electronic alteration of the frequency of the rectangular signal.

The frequency of the rectangular signal can also be varied electronically, as is explained by way of example with reference to FIG. 3. In this case, the perforated disc 6 illustrated in FIG. 2 is secured directly to the yarn-delivery roller so that, while retaining the light source 60 and photoelectric cell 61, a pulse repetition frequency is produced which is proportional to the yarn-delivery speed. Connected to the photoelectric cell 61 is a frequency-voltage converter 7, the output of which is connected to the first input of an adding amplifier 71. Connected to the second input of the adding amplifier 71 is a delta-voltage generator 72. The adding amplifier 71 is followed by a voltage-frequency converter 73 which is electrically connected to the frequency divider 20 (FIG. 1).

According to this arrangement, the frequency of the rectangular signal produced is converted by the frequency-voltage converter into a voltage proportional thereto and then altered by a small amount by adding to this voltage a second voltage which is produced in the delta-voltage generator 72 and which is relatively low and alters slowly, for example within 2 minutes, in delta form. Accordingly, the frequency of the output signal of the voltage-frequency converter 73 also alters in comparison with the frequency of the input signal entering the frequency-voltage converter 7, by a small amount.

The signal processing is explained below with reference to FIG. 1. The rectangular signal of variable frequency, which is produced by the signal generator 2 consisting of the device shown in FIG. 2 or of the device shown in FIG. 3 with a perforated disc 6 mounted directly on the yarn-delivery roller 4, is supplied to the frequency divider 20 and a frequency-voltage converter 8. Different divider ratios can be set in the frequency divider 20 depending on the circumference of the spinning rotor, as indicated in FIG. 1. It should be pointed out here that only one of each of the components 2, 20 and 8 is present on each open-end spinning machine. Therefore, the production of the rectangular signal of variable frequency is only of minor importance as regards cost, in relation to the individual spinning stations. On the other hand, the components mentioned below are present at each spinning station.

The rectangular signal emerging from the frequency divider 20 reaches a multiplier 21 which electrically multiplies the rectangular signal by the amplified yarn signal originating from the sensor 1. The multiplication product passes to a demodulator 22, in which the rectangular signal is largely eliminated. Following the demodulator 22 is a selective filter 23 which is adjusted to the differential frequency between rectangular-signal frequency and moire frequency. The filter 23, however, does not only deliver a signal when there is a moire effect in the spun yarn but also responds to frequencies which are included in the normal irregularities in the yarn. The signal delivered in this case, however, is considerably lower.

An improvement in the signal-to-noise ratio and, hence, a greater certainty of detection of a moire effect is obtained if the differential-frequency signal formed is compared, before the further processing, with a threshold value which is designated as the second threshold value. This threshold value is referred to as the second threshold value so as to distinguish it from the threshold value fed in at the end of the system which is discussed below. The comparison takes place in a comparator 24. In order to adapt the method and the apparatus for use for a wider range of yarn counts, the amplitude of this second threshold value is derived from the yarn signal, in that the comparator 24 is connected to the sensor 1 through an amplifier 9. The amplitude of the second threshold value may, however, also be derived from the speed of rotation of the yarn-delivery roller 4, as a result of which it is possible to use the apparatus for a wide range of speeds in the thread delivery. In this case, the threshold voltage is supplied to the comparator 24 through the frequency-voltage converter 8 (broken line). Likewise, it is also possible, instead, to adjust the amplitude of the threshold value by hand.

The signal components leaving the comparator 24 reach a pulse shaper 25 in which the filtered differential-frequency signal is subjected to a pulse shaping. The shaped pulse train is subsequently integrated in an integrator 26, at the output of which a voltage builds up which depends on the extent of the moire effect. The integrated differential-frequency signal is supplied to a comparator 27 in which it is compared with a threshhold value, the height of which may appropriately be derived from the speed of rotation of the yarn-delivery roller 4, in order to obtain a greater certainty of detection of a wider range of yarn counts and wider range of yarn-delivery speeds. For this purpose, the comparator 27 is electrically connected to the frequency-voltage converter 8. The threshold value can, however, also be adjusted by hand if required. If this threshold value is exceeded by the integrated differential-frequency signal, and thus a specific extent of the moire effect is reached, the comparator 27 delivers a pulse to a component characterized, for example, by a switch or relay 28 which can be used to switch off the spinning station or to actuate an indicating device.

While a preferred embodiment of the invention has been described using specific terms, such description is for illustrative purposes only, and it is to be understood that changes and variations may be made without departing from the spirit or scope of the following claims.

What is claimed is:

1. A method of detecting faulty working of spinning units of an open-end spinning machine by monitoring faults occuring in yarn being produced by open-end spinning machines, a fault sensing device positioned between a spinning compartment and a bobbin which receives the yarn, said fault sensing device generating an electrical signal responsive to faults occurring in said yarn, said method comprising the following steps:
    (a) generating a signal of predetermined frequency corresponding to the speed of delivery of said yarn from open-end spinning machine,
    (b) electrically multiplying said signal generated by said fault sensing device by said signal of predetermined frequency for generating a differential-frequency signal,
    (c) filtering and shaping said differential-frequency signal, and
    (d) integrating and comparing said filtered and shaped signal with a preset threshold value for producing a signal indicating faulty working of said spinning unit.

2. The method as set forth in claim 1 wherein the signal of a predetermined frequency is a rectangular signal.

3. The method as set forth in claim 2 wherein the frequency of the rectangular signal is derived from the speed of rotation of a thread delivery roller forming part of said open-end spinning machine.

4. The method as set forth in claim 2 further comprising the step of periodically altering the frequency of the rectangular signals.

5. The method as set forth in claim 4 wherein the frequency of the rectangular signal is varied mechanically.

6. The method as set forth in claim 4 wherein the frequency of the rectangular signal is varied electronically.

7. The method as set forth in claim 1 further comprising the step of comparing said filtered differential frequency signal with a second threshold value prior to shaping said differential frequency signal.

8. The method as set forth in claim 7 wherein the amplitude of the second threshold value is derived from said fault sensing device.

9. The method as set forth in claim 7 wherein the amplitude of the second threshold value is derived from the speed of rotation of a thread delivery roller forming part of said open-end spinning machine.

10. The method as set forth in claim 1 wherein the amplitude of said preset threshold value is derived from the speed of rotation of a thread delivery roller forming part of said spinning machine.

11. The method as set forth in claim 1 wherein said fault sensing device generates said electrical signal by measuring the tension in the yarn extending between said spinning compartment and said bobbin for sensing changes therein resulting from changes in the yarn mass.

12. A method of detecting periodically recurring faults in yarn produced on a spinning machine for determining when components of said spinning machine are not functioning properly, said spinning machine having rotating components thereon which rotate at a rate corresponding to the speed that the yarn is being delivered from said spinning machine, comprising the following steps:
  (a) monitoring the yarn being produced on said spinning machine and generating an electrical signal indicating the presence of faults therein,
  (b) generating a signal of predetermined frequency corresponding to the speed of delivery of said yarn from said spinning machine,
  (c) electrically multiplying said electrical signal with said signal of predetermined frequency for generating a differential frequency signal,
  (d) utilizing said differential signal to produce a modified signal for being compared with a preset threshold value signal, and
  (e) comparing said modified signal produced from said differential signal with said threshold value signal and generating a threshold exceeding signal when said threshold value signal is exceeded.

13. An apparatus for detecting the faulty working of spinning units of an open-end spinning machine by monitoring the faults in yarn as it is fed from a spinning compartment to a winding bobbin, said apparatus comprising:
  (a) means for monitoring said yarn as it is fed from said spinning compartment to said winding bobbin and generating an electrical signal responsive to faults occurring in said yarn,
  (b) means for generating a signal of predetermined frequency responsive to the rate that said yarn is being fed from said spinning compartment,
  (c) means for electrically multiplying said signal produced by said monitoring means by said signal of predetermined frequency producing a differential-frequency signal,
  (d) means for generating a signal of a preset threshold value,
  (e) means for modifying said differential frequency signal for being compared with said signal of preset threshold, and
  (f) a comparator means comparing said modified differential-frequency signal with said threshold signal and generating a signal when said modified differential-frequency signal exceeds said threshold signal.

14. The apparatus as set forth in claim 13 wherein said spinning machine includes a yarn delivery roller interposed between said spinning compartment and said winding bobbin and wherein said means for generating a signal of predetermined frequency comprises:
  (a) a perforated disc connected to said yarn delivery roller for being rotated therewith,
  (b) a light source positioned on one side of said perforated disc, and
  (c) a photoelectric cell positioned on the other side of said perforated disc which generates an electrical signal corresponding to the speed of rotation of the yarn delivery roller.

15. The apparatus as set forth in claim 13 wherein said spinning machine includes a yarn delivery roller interposed between said spinning compartment and said winding bobbin and wherein said means for generating a signal of predetermined frequency comprises:
  (a) a slotted disc connected to said yarn delivery roller for being rotated therewith,
  (b) a magnetic sensor positioned adjacent said slotted disc for generating an electrical signal corresponding to the speed of rotation of said slotted disc.

16. The apparatus as set forth in claim 14 further comprising:
  a cone-gear drive means for connecting said perforated disc to said yarn delivery roller.

17. The apparatus as set forth in claim 15 further comprising:
  cone gear means for connecting said slotted disc to said yarn delivery roller.

18. An apparatus for detecting faulty working of spinning units as set forth in claim 13 wherein said means for generating a signal of predetermined frequency responsive to the rate that said yarn is being fed from said spinning compartment comprises:
  (a) a rotatable member being driven at a rate corresponding to the rate of delivery of yarn from said spinning compartment,
  (b) means for generating an electrical signal having a frequency corresponding to the rate of rotation of said rotatable member, and
  (c) a frequency voltage converter means for modifying said signal corresponding to said rate or rotation of said rotatable member,
  (d) a delta voltage generator means producing a varying electrical signal,
  (e) an amplifier means connected to said frequency voltage converter and said delta voltage generator producing a varying output voltage, and
  (f) a voltage-frequency converter means connected to an output of said amplifier means generating a varying frequency signal corresponding to said varying output voltage.

19. The apparatus as set forth in claim 13 wherein said means for modifying said differential frequency signal comprises:
  (a) a filter means connected to the output of said means for electrically multiplying said signal for filtering said differential-frequency signal,
  (b) means for generating a second threshold signal, and
  (c) second comparator means for comparing said filtered differential-frequency signal with said second threshold signal and producing a signal having an improved signal-to-noise ratio.

* * * * *